United States Patent [19]

Busse et al.

[11] Patent Number: 4,760,066

[45] Date of Patent: Jul. 26, 1988

[54] METHOD FOR TREATING HUMAN TUMOR CELL METASTASIS

[75] Inventors: Wolf-Dieter Busse, Wuppertal, Fed. Rep. of Germany; Kenneth V. Honn, Grosse Point Woods, Mich.; Eike Möller; Friedel Seuter, both of Wuppertal, Fed. Rep. of Germany

[73] Assignee: Wayne State University, Detroit, Mich.

[21] Appl. No.: 928,614

[22] Filed: Nov. 4, 1986

Related U.S. Application Data

[63] Continuation of Ser. No. 420,642, Sep. 21, 1982, abandoned, which is a continuation-in-part of Ser. No. 400,878, Jul. 22, 1982, abandoned, which is a continuation of Ser. No. 251,864, Apr. 7, 1981, abandoned.

[51] Int. Cl.$^4$ .................... A61K 31/52; A61K 31/415
[52] U.S. Cl. .................................... 514/264; 514/404
[58] Field of Search ............................... 514/404, 264

Primary Examiner—Jerome D. Goldberg
Attorney, Agent, or Firm—Ian C. McLeod

[57] ABSTRACT

A therapeutic method for reducing metastasis is disclosed. The method involves administering a therapeutically effective amount of 3-methyl-1-[2-(2-naphthyloxy)-ethyl]-2-pyrazolin-5-one or a pharmaceutically acceptable salt.

5 Claims, No Drawings

METHOD FOR TREATING HUMAN TUMOR CELL METASTASIS

This application is a continuation of pending U.S. application Ser. No. 420,642, filed Sept. 21, 1982, now abandoned; which is a continuation-in-part of Ser. No. 400,878, filed July 22, 1982, now abandoned; which in turn is a continuation of Ser. No. 251,864, filed Apr. 7, 1981, now abandoned.

BACKGROUND AND PRIOR ART

The primary goal of cancer treatment is treatment and eradication of the growth of the primary tumor. Concurrent with this treatment it is necessary to prevent metastasis, which can be defined as separation of primary tumor cells and their subsequent penetration into the lymphatic system or blood vessels for dissemination. Such dissemination may occur by adhesion to and subsequent penetration through the endothelial walls, establishment of secondary tumors in the perivascular tissues and eventual spread of the tumor cells to more distant sites. Although much is known about the clinical manifestations of the metastatic process, little is understood about the biochemical, immunologic, genetic, and hormonal mechanisms involved in metastasis. Thus metastasis can be considered as a single phenomenom represented by an intricate series of events.

Because of the importance of both treatment of primary tumor growth and prevention of metastasis, cancer researchers have undertaken extensive research to define the interactions involved in tumor growth and metastasis.

One of the biological properties which tumor cells appear to possess is the ability to interact with and to attach to host blood platelets, enhancing the potential of the tumor to lodge in the microvasculature and adhere to vascular endothelium. Alternatively, it has been suggested that following lodging of the tumor cells, the cells may initiate the formation of surrounding protective platelet thrombi. For successful metastasis to occur, the metastatic cells must first lodge and adhere to the vascular endothelium and remain intravascular until it infiltrates into the surrounding tissue.

Because of the similarities of the process involved in the lodging and adherance of the tumor cells to the endothelium and the formation of non-tumor thrombi, many investigators have concluded that platelets are involved in some fashion. Because of this platelet involvement, numerous investigations have been undertaken to determine the effect of anticoagulant therapy on metastasis. The investigations referred to below involved the administration of anticoagulant compounds which are potent inhibitors of platelet aggregation. The results to date have been ambivalent.

Heparin has been reported to both decrease and increase metastasis, especially pulmonary. [See *Cell Biol. Intl. Rep.* 2: 81–86 (1963) and *Arch. Surg.* 91: 625–629 (1965)]. Aspirin has produced mixed results [See *Eur. J. Cancer* 8: 347–352 (1972) and *Intl. J. Cancer* 11: 704–718 (1973)]. Warfarin has been demonstrated to produce significant antimetastatic effects after intervenous injection of tumor cells and in spontaneously metastasizing tumors [See *Cancer* 35: 5–14 (1975) and *Cancer Res* 37: 272–277 (1971)]. It has been shown that metastasis induced by intravenous administration of B-16$_a$ melanoma cells can be prevented by administration of the anticoagulant agent prostacyclin [See *Cell Biol.* 87: 649 (1980)].

For a review of the use of anticoagulants in tumor therapy, see M. B. Donati, et al., *Malignancy and the Hemostatic System*, pp. 103–120, Raven Press, 1981.

It has been suggested that the use of anticoagulant therapy has been less than satisfactory in part because of the lack of specificity of the anticoagulant agents used and the fact that some of the agents produce effects on the tumor cells themselves which may overall, negate the desired effect on blood platelets, and hence metastasis.

According to the present invention, the compound 3-methyl-1-[2-(2-naphthyloxy)-ethyl]-2-pyrazolin-5-one, disclosed and claimed as a therapeutically efficacious antithrombotic agent in U.S. Pat. No. 4,053,621, has been found to be a potent antimetastatic agent without treating the tumor per se.

SUMMARY OF THE INVENTION

The present invention is directed to a therapeutic method for reducing metastasis in a mammal. The method involves administering to the mammal a therapeutically effective amount of 3-methyl-1-[2-(2-naphthyloxy)-ethyl]-2-pyrazolin-5-one without treating the tumor per se.

DETAILED DESCRIPTION OF THE INVENTION

As disclosed in U.S. Pat. No. 4,053,621, the methyl pyrazolin compound used in the present invention (represented by Formula I below), can be prepared by various routes of synthesis as illustrated below. According to Process A, 2-(2-naphthyloxy)-ethylhydrazine is reacted with an acetoacetic acid derivative; according to Process B, 3-methylpyrazolin-5-one is reacted with a 2-(2-naphthyloxy)ethyl derivative; according to Process C, 2-(2-naphthyloxy)-ethylhydrazine is reacted with a tetrolic acid derivative.

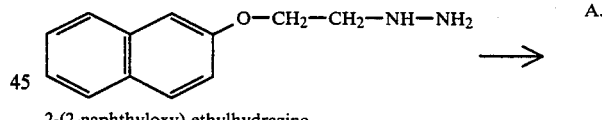

2-(2-naphthyloxy)-ethylhydrazine

+

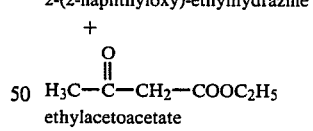

ethylacetoacetate

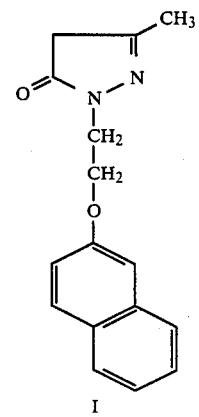

I

-continued

3-methylpyrazolin-5-one
+
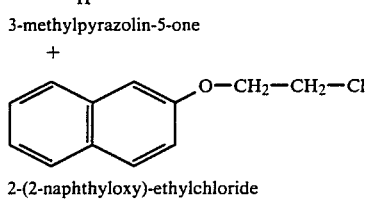
2-(2-naphthyloxy)-ethylchloride

→ B.

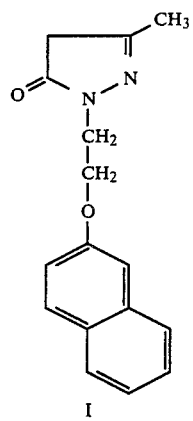
I

C.
$H_5C_2O—\overset{\overset{O}{\|}}{C}—C\equiv C—CH_3$
ethyl-2-butynate
+
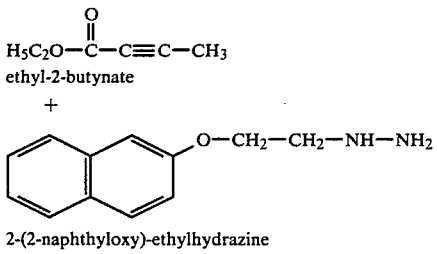
2-(2-naphthyloxy)-ethylhydrazine

→

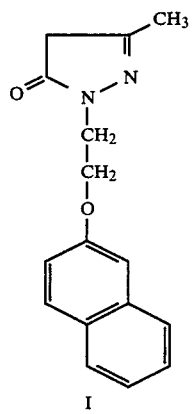
I

Diluents which can be used include all inert organic solvents, optionally diluted with water, e.g., hydrocarbons such as benzene and toluene; halohydrocarbons such as methylene chloride; alcohols such as methanol and ethanol; and organic basis such as pyridine and picoline.

Basic or acid condensation agents can be used, and the reaction temperature can be varied between 10° and 200° C. The compound can be easily purified by conventional means by recrystallization from a suitable solvent.

In the present specification the expression "diluent or carrier" means a pharmaceutically acceptable non-toxic substance that when mixed with the active ingredient or ingredients renders it suitable for administration. The expression preferably excludes water and low-molecular weight organic solvents commonly used in chemical synthesis, except in the presence of other pharmaceutically necessary ingredients such as salts in correct quantities to render the composition isotonic, buffers, surfactants, coloring and flavoring agents, and preservatives. Examples of suitable solid and liquid diluents and carriers are the following: water containing buffering agents which can be rendered isotonic by the addition of glucose or salts; non-toxic organic solvents; such as paraffins, vegetable oils; alcohols; glycols; natural ground rock (for example kaolins, aluminas, talc or chalk); synthetic rock powders (for example highly dispersed silica or silicates); and sugars.

Oral administration can be effected utilizing solid and liquid dosage unit forms such as powders, tablets, dragees, capsules, granulates, suspensions, solutions and the like. Where appropriate, dosage unit formulations for oral administration can be microencapsulated to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Stabilizers, preservatives and emulsifiers can also be added.

Generally the parenteral dosage will be from 0.01 to 50 mg/kg, preferably from 0.1 to 10 mg/kg, of body weight per day, and the oral dosage form will be from 0.1 to 500 mg/kg, preferably 0.5 to 100 mg/kg, of body weight per day.

The following procedure was used to determine the antimetastatic properties of 3-methyl-1-[2-(2-naphthyloxy)-ethyl]-2-pyrazolin-5-one without treating the tumor per se. The test protocol utilized two unrelated murine tumor types (a melanoma and a carcinoma) to minimize the possiblity the the results obtained are "unique" to a single tumor type. Both of these tumors are routinely used for basic studies on the mechanism of metastasis without treating the tumor per se.

A. IN VIVO MAINTENANCE OF TUMOR LINES

Subcutaneous B-16 amelanotic melanoma (B-16$_a$) and Lewis Lung carcinoma (3LL) were obtained from the Division of Cancer Treatment, (NCI), Animal and Human Tumor Bank, Mason Research Institute, Worcester, Mass. Both types of tumors were passaged four times after receipt. Passage involved subcutaneous implantation of a 2×2 mm tumor dice in the right axillary region (using a 13 gauge trocar needle) of male, syngeneic host mice [(C57BL/6J; Jackson Laboratory Strain]. The host mice were between 17–22 g (approximately 28 days old) and housed under identical conditions of photoperiod, feeding regimen, temperature, etc.

The transplanted tumors were allowed to grow in the syngeneic host mice for approximately 14 days following implantation.

B. ISOLATION AND SUSPENSION OF TUMOR CELLS

Tumor cells were then obtained from the host mice by aseptic removal and dispersed using sequential collagenase digestion, as described below. The removed tumors were diced (4×4 mm) and the diced tissue divided (approximately 500 mg/flask) between 6-8 sterile polycarbonate Erhlenmeyer flasks. A 10 ml portion of a "tumor dispersion solution" (TDS) was added to each flask.

The TDS was prepared by mixing together Composition A and Composition B described below.

| COMPOSITION A (based on 1 liter) | |
|---|---|
| 9.5 g/l | Sterile Eagle's Minimum Essential Medium (MEM) (Commercially available from Gibco, Grand Island, New York) |
| 10 ml/l | Nonessential Amino Acids (Gibco) |
| 10 ml/l | Sodium pyruvate |
| 0.35 g/l | Sodium bicarbonate (15 mM) |
| 5.9 g/l | HEPES (25 mM) (an organic buffer; commercially available from Sigma Chemical, St. Louis, Missouri) |
| 150 Units/ml | Penicillin |
| 100 μg/ml | Neomycin sulfate |

The antibiotics were added to ensure that bacterial contamination did not occur.

Composition B is a dry mixture containing collagenase low in clostripain and other proteolytic activity; deoxyribonuclease (DNase) to dissolve deoxyribonucleoprotein released from damaged cell nuclei; limabean or soybean trypsin inhibitors to exclude any residual tryptic activity; human serum albumin to eliminate non-specific protease activity and absorb peroxy and hydroperoxy fatty acids liberated from damaged membranes.

| COMPOSITION B | |
|---|---|
| | Weight/ml Composition A |
| Collagenase (Worthington type III) | 1 mg/ml |
| DNase I (Sigma Chemical) | 50 μg/ml |
| Soybean trypsin inhibitor (Worthington) | 100 μg/ml |
| Human serum albumin (fatty acid-free; Sigma Chemical) | 10 mg/ml |

Composition B was weighed out and placed in a flask and 100 ml of Composition A added.

The diced tissue in the TDS was then dispersed (30 min., 37° C.) under air in a Dubnoff Metabolic Shaker (90 oscillations/minute). Supernatants were collected through cheesecloth into sterile 50 ml polycarbonate round bottom centrifuge tubes and centrifuged for 10 minutes (25° C.) at 900 rpm (100 xg) in a Sorvall SS-34 rotor. Following centrifugation, the supernatant fraction was discarded. The solid cellular matter (pellets) obtained were washed twice with MEM solution, resuspended in MEM and held at 4° C.

A 10 ml portion of TDS was added to the remaining diced tissue and the tissue incubated in a metabolic shaker as described hereinabove, except for a period of 60 minutes. The centrifugation was repeated and the resuspended cells were combined.

The cell viability was determined by the vital dye exclusion method [See *Exptl. Cell Res.* 13: 341-347 (1957)]. The cell count was determined in a hemocytometer. The stromal cell contamination, e.g. macrophages, red blood cells, etc. was determined by visual examination under a microscope. The final cell suspension obtained consisted of greater than 99 percent monodispersed cells with approximately 25 percent host stromal cell contamination. Typical yields from a 3.0 g B-$16_a$ or 3LL tumor ranged between $9 \times 10^8$ and $1.3 \times 10^9$ viable tumor cells.

The final cell suspensions were then subjected to centrifugal elutriation for final separation of the tumor cells. In centrifugal elutriation, cells are subjected to two opposing forces within a separation chamber; a centrifugal field generated by a spinning rotor and a counterflow of fluid in the opposite (centripatal) direction. A sample suspended in a medium enters the separation chamber. Each cell tends to migrate to a zone where its sedimentation rate is exactly balanced by the flow rate of the fluid through the separation chamber. The chamber's geometry produces a gradient of flow rates from one end to the other; cells with a wide range of different sedimentation rates can be held in suspension. By increasing the flow rate of the elutriating fluid (separation medium) in steps, or by decreasing the rotor speed, successive populations of relatively homogenous cell sizes can be washed from the chamber. Each population will contain cells which are larger or more dense (i.e. faster sedimenting) than those of the previous fraction.

Centrifugal elutriation was accomplished by suspending the tumor cells in a "Tumor Resuspension Solution" (TRS), having the following composition, based on one liter.

| 9.5 g/l | Sterile Eagle's Minimum Essential Medium (MEM) (Gibco) |
|---|---|
| 10 ml/l | Nonessential Amino Acids (Gibco) |
| 10 ml/l | Sodium pyruvate |
| 0.35 ml/l | Sodium bicarbonate (15 mM) |
| 5.9 g/l | HEPES (25 mM) (Sigma Chemical) |
| 150 Units/ml | Penicillin |
| 100 μg/ml | Neomycin sulfate |

The suspension was elutriated using a Beckman JE-6 elutriator rotor operating at 2000 rpm in a Beckman J-2-21 centrifuge at 25° C.

A separation medium of Hank's Balanced Salt Solution was pumped through the system using a Cole Palmer Master Flex pump with a No. 7014 pump head. The pump control box was modified with a 10 turn potentimeter [See *Anal. Biochem* 98: 112-115 (1979)]. The flow rate was measured with a Brooks double-ball flow value.

Hank's Balanced Salt Solution was prepared by preparing a 900 ml solution having the following composition and mixing with $CaCl_2.2H_2O$ as described below.

80 g NaCl
4 g KCL
0.98 g $MgSO_4$
0.48 g $Na_2HPO_4$
0.60 g $KH_2PO_4$

A 1.85 g portion of $CaCl_2.2H_2O$ was made up to 100 ml solution, and mixed together with the 900 ml described above.

Approximately $1 \times 10^9$ cells were injected through an in-line "Y" fitting into the mixing chamber. After a 15 minute equilibration time, cell debris was eluted at a flow rate of 9.0–10 ml/min. Tumor cells were eluted in 6 fractions of 50 ml each at flow rates from about 12–18 ml/min. Fractions 2–5 containing tumor cells were combined, recentrifuged (100×g) and resuspended in 1–2 ml of the TRS described above. Recoveries were generally between 70–75 percent of the cells injected into the mixing chamber.

C. EFFECTS OF 3-METHYL-1-[2-(2-NAPHTHYLOXY)-ETHYL]-2-PYRAZOLIN-5-ONE ON TUMOR CELL METASTASIS AND GROWTH

The B-16$_a$ melanoma and Lewis Lung carcinoma cells thus obtained were used to test the antimetastatic of the methyl pyrazolin compound without treating the tumor per se, as described below.

Metastasis

As indicated earlier, metastasis is a single phenomenom represented by an intricate series of events. At present, there are two "model" systems widely used in studying in vivo metastasis. The first model system involves the subcutaneous injection of tumor cells into the animal. Subcutaneous injection of tumor cells and subsequent development of a primary tumor, followed by spontaneous metastasis is considered to be "full" metastasis. Another model system involves the injection of tumor cells via the tail vein. Considering the complexity of metastasis, it is recognized that tail vein injection is an artificial and only partial model system, since it represents events occuring in the latter portion of metastasis. However, the tail vein model system is recognized as being extremely useful in standardizing experimental conditions. [See *Methods in Cancer Research*, Chapter VII, Academic Press, Inc., 1978.]

Control (untreated) C57B1/6J mice were tested for full metastasis by the following procedure. Cell suspensions of B-16$_a$ and 3LL carcinoma cells obtained as described in A and B above, were injected (26 gauge needle, 0.2 ml) subcutaneously into the right axillary region of the male C57BL/6J mice. Varying amounts of cell suspensions in the range of $1\times10^5$ to $1\times10^6$ cells were injected. Partial metastasis experiments were conducted by injecting the control (untreated) mice with tumor cells via the tail vein. The animals were housed under identical conditions of temperature, photoperiod, feeding, etc. After an observation period of from 17 to 30 days, the animals used in the full metastasis and partial metastasis were killed and the lung, liver, kidney, spleen and brain tissue was removed.

The removed tissue was fixed in Bouin's solution. The number of metastatic nodules in each organ was determined using a Bausch and Lomb Stereo Zoom Microscope. Examination of the control mice for metastatic nodules indicated that 100 percent of the animals are positive for metastatic lung tumors; the incubation time to produce such metastasis was betwee 17–21 days and between 23–30 for the 3LL and B-16$_a$ tumor cells, respectively. No visible nodules were observed in the liver, kidney, spleen or brain tissue.

The effect of 3-methyl-1-[2-(2-naphthyloxy)-ethyl]-2-pyrazolin-5-one on metastasis from tail vein injection of tumor cells and full metastasis from subcutaneous injection of tumor cells is shown in Examples 1 and 2 respectively.

EXAMPLE 1

A 3 mg portion of 3-methyl-1-[2-(2-naphthyloxy)ethyl]-2-pyrazolin-5-one was suspended in 0.6 ml absolute ethyl alcohol. The suspended methyl pyrazolin was dissolved by adjusting the suspension to a pH of 9.5 with NaOH. The final concentration of the methyl pyrazolin was achieved by dilution of the solution with normal saline (0.9 percent NaCl).

Syngeneic C57BL/6J host mice were injected on a daily basis, with 0.02 and 0.08 mg/mouse of the methyl pyrazolin compound (subcutaneously) for a period of 3 days.

On the fourth day, the pretreated mice (and control mice) were injected via the tail vein with a $5\times10^4$ B-16$_a$ tumor cell suspension prepared as described hereinbefore. The control mice and treated mice were housed under identical conditions of temperature, photoperiod, feeding, etc. The mice were killed 14 days after tail vein injection of the tumor cells and the lung tissue examined. The effect of injecting mice with the methyl pyrazolin compound one hour before B-16$_a$ tumor cell injection was also determined.

As seen by the data summarized in Table 1, administration of the methyl pyrazolin compound is efficacious in drastically reducing lung tumor colonies, i.e., metastasis, at both 0.02 and 0.08 mg levels.

It has been suggested that the present methyl pyrazolin compound stimulates prostacyclin release. [See *The Lancet*, pp. 518–520 (Mar. 10, 1979)]. The antithrombotic activity of prostacyclin is believed to be mediated by increasing platelet levels of cyclic adenosine-3',5'-cyclic phosphoric acid (cAMP). It is also known that compounds known as phosphodiesterase inhibitors slow the breakdown of cAMP. Therefore, by slowing the breakdown of cAMP, phosphodiesterase inhibitors would be expected to potentiate the anti-thrombotic action of an antithrombotic agent, acting through this mechanism. Because platelets may also be involved in the mechanism of metastasis, the effect of a well-known phosphodiesterase inhibitor, theophylline, was tested for its potential synergism with the methyl pyrazolin compound.

Although the results indicate that the anti-metastatic effect may have been enhanced by theophylline, because of the standard error involved in the experiment, synergism was not firmly established.

TABLE 1

Effect of 3-methyl-1-[2-(2-naphthyloxy)-ethyl]-2-pyrazolin-5-one on Metastasis from Tail Vein Injected B-16$_a$ Amelanotic Melanoma Cells[a]

| Treatment | | Lung Tumor Colonies |
|---|---|---|
| Control | | 181 ± 45[b] |
| 0.02 mg | 3-methyl-1-[2-(2-naphthyloxy)-ethyl]-2-pyrazolin-5-one[c] | 19.3 ± 7.5 |
| 0.08 mg | 3-methyl-1-[2-(2-naphthyloxy)-ethyl]-2-pyrazolin-5-one[c] | 2.7 ± 1.3 |
| Theophylline 200 μg[d] | | 165 ± 38 |
| Theophylline 200 μg + 0.08 3-methyl-1-[2-(2-naphthyloxy)-ethyl]-2-pyrazolin-5-one[d] | | 33.6 ± 18 |
| 0.08 mg | 3-methyl-1-[2-(2-naphthyloxy)-ethyl]-2-pyrazolin-5-one[d] | 65 ± 36 |

[a] $5 \times 10^4$ cells injected intravenously in 50 μl.
[b] $\bar{x}$ ± SEM; n = 6.
[c] Animals pretreated daily (3 days) before tumor cell injection.
[d] Injected 1 hour prior to tumor cells.

EXAMPLE 2

The effect of administration of the methyl pyrazolin compound for an extended period of time, on the number of metastatic lung colonies of B-16$_a$ and Lewis Lung carcinoma was determined as described below.

A 3 mg portion of 3-methyl-1-[2-(2-naphthyloxy)ethyl]-2-pyrazolin-5-one was dissolved in 0.6 ml ethyl alcohol and the solution adjusted to a pH of 9.5 with concentrated NaOH.

Syngeneic C57BL/6J host mice were injected subcutaneously with a $1.8 \times 10^5$ B-16$_a$ cell suspension, prepared as described hereinbefore. Another series of syngeneic C57BL/6J host mice were injected subcutaneously with a $1 \times 10^5$ Lewis Lung carcinoma cell suspension, obtained as described hereinbefore. The day following tumor cell injection, the mice were injected subcutaneously for 28 days, with a single daily dose of either 0.01 or 0.08 mg of the methyl pyrazolin compound. The control mice and the treated mice were housed under identical conditions of temperature, photoperiod, feeding, etc. The mice injected with B-16$_a$ tumor cells were killed 25 days after injection of the tumor cells; the mice injected with Lewis Lung carcinoma cells were killed 21 days after injection of the tumor cells.

Experimental data obtained on the examined lung tissue are summarized in Table 2 below.

TABLE 2

Effects of 3-methyl-1-[2-(2-naphthyloxy)-ethyl]-2-pyrazolin-5-one on Spontaneous Metastasis from Injected B-16$_a$ Amelanotic Melanoma[a] and Lewis Lung Carcinoma[b]

| Treatment | | Lung Tumor Colonies B-16$_a$ Cells | Lung Tumor Colonies Lewis Lung Cells |
|---|---|---|---|
| Control | | 14.1 ± 3.1[c] (12/12) | 34.5 ± 6.4 (12/12)[c] |
| 0.01 mg | 3-methyl-1-[2-(2-naphthyloxy)-ethyl]-2-pyrazolin-5-one | 1.7 ± 0.7 (7/12) | — |
| 0.02 mg | 3-methyl-1-[2-(2-naphthyloxy)-ethyl]-2-pyrazolin-5-one | 2.5 ± 0.9 (7/12) | — |
| 0.04 mg | 3-methyl-1-[2-(2-naphthyloxy)-ethyl]-2-pyrazolin-5-one | 3.1 ± 0.8 (8/12) | — |
| 0.08 mg | 3-methyl-1-[2-(2-naphthyloxy)-ethyl]-2-pyrazolin-5-one | 1.4 ± 0.8 (5/12) | 0.8 ± 0.5 (2/12) |

[a]$1.8 \times 10^5$ cells injected subcutaneously.
[b]$1 \times 10^5$ cells injected subcutaneously.
[c]Number of metastatic tumor colonies on bilateral lung surface; $\overline{X}$ ± SEM.
[d]Injected daily subcutaneously in 0.2 ml.

As shown by the test data summarized in Table 2, the number of metastatic lung colonies of both B-16$_a$ melanoma and 3LL carcinoma are drastically reduced by administration of the methyl pyrazolin compound.

With respect to the B-16$_a$ melanoma metastasis, a dosage level of 0.01 mg appeared to be almost as effective as a dosage level of 0.08 mg.

As indicated earlier, subcutaneous injection of tumor cells and subsequent development of a primary tumor, followed by spontaneous metastasis, is considered "full" metastasis. Because the procedure of Example 2 involved full metastasis, there were a lesser number of lung tumor colonies present in the control animals of Example 2 than in the control animals of Example 1, which involved development of metastasis from tail vein injection of tumor cells. However, the data in both Example 1 and Example 2 indicate that the methyl pyrazolin compound possesses strong anti-metastasis activity without treating the tumor per se.

What is claimed is:

1. A method for reducing interaction between blood platelets and malignant tumors present in the blood and resulting attachment of the tumors with the platelets in blood vessels in a mammal which comprises:
    administering to a mammal in need thereof an effective amount of
    3-methyl-1-(2-(2-naphthloxy)-ethyl-2-pyranolin-5-one which reduces the interaction between the platelets and the tumors and resulting attachment of the tumors with the platelets in the blood vessels without treating the tumors to thereby interfere with the metastatic cascade in the mammal and wherein in vitro the
    3-methyl-1-(2-(2-naphthyloxy)-ethyl-2-pyranolin-5-one prevents aggregation of tumor cells and platelets.

2. The method as claimed in claim 1 wherein the administration is oral.

3. The method as claimed in claim 1 wherein the administration is parenteral.

4. The method of claim 1 wherein in addition theophylline is administered to the mammal in an effective amount which is antimetastatic with the 3-methyl-1-(2-(2-naphthyloxy)-ethyl-2-pyranolin-5-one.

5. A method as claimed in claim 1 wherein the tumor is produced by B-16 amelanotic melanoma or Lewis Lung carcinoma in mice as the mammal.

* * * * *